United States Patent
Cricchio et al.

[11] 3,933,800
[45] Jan. 20, 1976

[54] NEW 3-FORMYLRIFAMYCIN SV DERIVATIVES

[75] Inventors: Renato Cricchio, Varese; Giancarlo Lancini, Pavia, both of Italy

[73] Assignee: Gruppo Lepetit S.p.A., Milan, Italy

[22] Filed: Oct. 23, 1974

[21] Appl. No.: 517,272

Related U.S. Application Data

[63] Continuation of Ser. No. 256,297, May 24, 1972, abandoned.

[30] Foreign Application Priority Data

June 7, 1971 Italy .................................. 25493/71
June 24, 1971 Italy .................................. 89607/71

[52] U.S. Cl. .......... 260/239.3 P; 424/244; 424/250; 424/263; 424/267; 424/272; 424/274; 424/275; 424/278
[51] Int. Cl.² ............... C07D 491/04; C07D 521/00
[58] Field of Search .............................. 260/239.3 P

[56] References Cited
UNITED STATES PATENTS

3,342,810    9/1975    Maggi et al. .................. 260/239.3 P

*Primary Examiner*—Henry R. Jiles
*Assistant Examiner*—Robert T. Bond
*Attorney, Agent, or Firm*—Theodore Post; C. Kenneth Bjorh

[57] ABSTRACT

The present invention is concerned with new derivatives of 3-formylrifamycin SV. More particularly the invention relates to O-substituted oximes of 3-formylrifamycin SV of formula I.

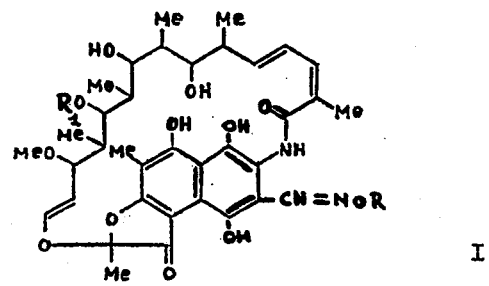

wherein R is selected from the group consisting of alkyl of at least 2 carbon atoms, alkenyl, alkynyl, cycloalkyl, alkoxyalkyl, cycloalkoxyalkyl, hydroxyalkyl, carboxyalkyl, carboalkoxyalkyl, carbamylalkyl, cyanoalkyl, nitroalkyl, aryloxyalkyl, aralkoxyalkyl, heterocycloxyalkyl, aminoalkyl, mono- and di-lower alkylaminoalkyl, substituted benzyl, mono- or poly-aryl substituted $C_2$–$C_8$ alkyl and lower alkyl substituted with mono- or polynuclear heterocyclic rings containing at least one 1 to 3 heteroatom selected from oxygen, nitrogen and sulfur, with the exclusion of morpholine; $R_1$ is H or $CH_3CO$; and the derivatives of the same oximes hydrogenated in at least one of the positions 16, 17; 18, 19; and 28, 29. These compounds have antimicrobial activity.

6 Claims, No Drawings

NEW 3-FORMYLRIFAMYCIN SV DERIVATIVES

CROSS REFERENCE TO RELATED APPLICATION

This is a continuation of application Ser. No. 256,297, filed May 24, 1972, now abandoned.

BACKGROUND OF THE INVENTION

The present invention is concerned with O-substituted oxime derivatives of 3-formylrifamycin SV.

The oxime of 3-formylrifamycin SV and its O-methyl and O-morpholinoethyl derivatives are described in U.S. Pat. No. 3,342,810. These compounds although possessing a good antibacterial activity have practically no effect against bacteria which had become resistant to the other rifamycins, namely the most known and therapeutically useful 3-(4-methyl-1-piperazinyl-iminomethyl)-rifamycin SV (rifampicin).

It is well known by those who are expert in the antibiotic field that when a microorganism strain becomes resistant to a particular antibiotic drug, it is rather difficult to find another compound of the same antibiotic family which is capable to inhibit the growth of said resistant mutant. In some instances it is quite difficult to find compounds which are active against such a resistant strain even among the other different species of antibiotics.

We have surprisingly found that by substituting the hydrogen atom of the oximino group of 3-formylrifamycin SV oxime by an alkyl radical with at least 2 carbon atoms or some other suitable radical very promising compounds may be obtained which are able to exhibit at low concentrations the growth of strains resistant to the other rifamycins.

In particular, compounds of the invention display a good inhibiting effect against the rifampicin resistant *Staphylococcus aureus* strains. In representative experiments in vitro with the compounds of Examples 6, 8, 13, 16, 21, 23 and 25, the growth of a *Staphylococcus aureus Tour* strain, resistant to rifampicin, was inhibited by concentrations ranging from 1 to 5 µg/ml.

This particular activity is moreover coupled with a good general effect against the other microorganisms which are usually sensitive to the rifamycins.

The invention compounds are generally very active also against the usual Gram positive and Gram negative bacteria. In particular they show a remarkable activity against *Staphylococcus aureus*, *Streptococcus faecalis*, *Streptococcus hemolyticus* and *Diplococcus pneumoniae* strains. In these cases the minimum inhibiting concentration ranges from about 0.001 to about 0.5 µg/mg.

Another very important feature of the invention is the activity of certain of the compounds in inhibiting the activity of DNA polymerases.

SUMMARY OF THE INVENTION

The invention relates to O-substituted oximes of 3-formylrifamycin SV of formula I

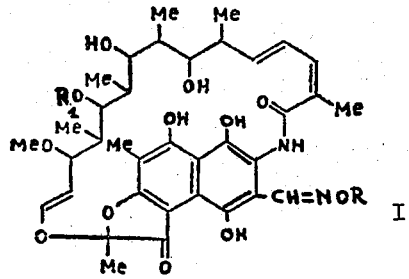

wherein R is selected from the group consisting of alkyl of at least 2 carbon atoms, alkenyl, alkynyl, cycloalkyl, alkoxyalkyl, cycloalkoxyalkyl, hydroxyalkyl, carboxyalkyl, carboalkoxyalkyl, carbamylalkyl, cyanoalkyl, nitroalkyl, aryloxyalkyl, aralkoxy-alkyl, heterocycloxyalkyl, aminoalkyl, mono- and di-lower alkyl-aminoalkyl, substituted benzyl, mono- or poly-aryl substituted $C_2$–$C_8$ alkyl and lower alkyl substituted with mono- or polynuclear heterocyclic rings containing at least one 1 to 3 heteroatom selected from oxygen, nitrogen and sulfur, with the exclusion of morpholine; $R_1$ is H or $CH_3CO$; and the derivatives of the same oximes hydrogenated in at least one of the positions 16, 17; 18, 19; and 28, 29.

Ordinarily the alkyl, alkenyl and alkynyl groups at a maximum will contain about 20 carbon atoms. Preferably, they will contain from about 4 to about 12 carbon atoms. These groups can be straight or branched. Further, the alkenyl groups can contain one or a plurality of double bonds and the alkynyl groups can contain one or a plurality of triple bonds.

The aryl and aralkyl groups are represented by aromatic groups containing 1 to 3 carbocyclic rings and can be unsubstituted or have one or more substituent groups positioned on the ring including, for example, lower alkyl of 1-4 carbon atoms, halogen, amino, mono- and dialkylamino, halo-lower alkyl, sulfo, fluorosulfonyl, sulfamido, cyano, carboxy, hydroxy, carbalkoxy, nitro and the like. The cycloalkyl groups ordinarily will contain from about 3 to about 18 carbon atoms.

Heterocyclic moieties for use in the present invention include the mono- or polynuclear heterocyclic ring groups containing at least one heteroatom selected from oxygen, nitrogen or sulfur. Morpholine is excluded when the heterocyclic is a substituent of a lower alkyl group.

A method for preparing the compounds of the invention consists in treating 3-formyltrifamycin SV or its 25-desacetyl and/or derivatives hydrogenated in at least one of the positions 16, 17; 18, 19; and 28, 29 in an organic solvent with a stoichiometric amount of an O-substituted hydroxylamine of the formula $NH_2$-O-R where R has the foregoing significance. After standing at room temperature for a period of time varying from 20 minutes to some hours, the crude compound is recovered by concentrating or evaporating the solvent. The purification of these derivatives does not represent a particular problem for those skilled in the organic field and is generally effected by crystallizing from a suitable solvent which for instance may be selected from lower alkanols or benzene.

The new compounds are colored solids soluble in the common organic solvent such as benzene, ethyl acetate, chloroform, dioxane, tetrahydrofuran and the like.

DESCRIPTION OF PREFERRED EMBODIMENTS

General method of preparation of the oximes is the addition to a tetrahydrofuran solution of 0.01 mole of 3-formyl-rifamycin SV or its 25-desacetyl or derivatives hydrogenated in at least one of the positions 16, 17, 18, 19, 28 and 29 of 0.01 mole of a preselected O-substituted hydroxylamine of the formula $NH_2$-O-R which is added at room temperature under stirring. After agitation for a period of time varying from 20 minutes to 3 hours a drop of the solution is tested by thin layer chromatography on silicagel to determine the disappearance of the staring compound and the formation of the desired rifamycin derivative end product. After complete disappearance of the carbonyl compound, the solution is concentrated to dryness and the crude compound recovered and purified by crystallizing from a solvent.

Table 1 presents the chemical-physical data of some representative O-substituted oximes of 3-formylrifamycin SV compounds of Formula I prepared by this technique wherein R is as set forth hereinabove. Unless stated otherwise, the depicted derivatives are to the 3-formylrifamycin SV compounds. The starting compound for preparing in Table 1 hydrogenated derivatives of the rifamycins of Formula I, e.g., 16, 17; 18, 19; and 28, 29 hexahydro-3-formylrifamycin SV, is obtained in the following way:

Twenty grams of rifamycin S suspended in 600 ml. of dry ethanol are hydrogenated in a Parr bomb with 2 g of $PtO_2$ and the catalyst for 3 hours at room temperature under a hydrogen pressure of about 5 atmospheres. After filtering off the catalyst the solution is evaporated to dryness and the crude product dissolved in tetrahydrofuran is maintained under stirring with 18 g. of $MnO_2$ at room temperature. The inorganic precipitate is filtered off and after concentration of the filtrate to a small volume the mixture is taken up with ethyl acetate (300 ml) and washed with water. The organic layer is dried over $Na_2SO_4$ and after evaporation gives 8 g. of hexahydrorifamycin S. M.p. 158°–160°C (from methanol). This product is then converted to the corresponding 3-formyl derivative by following the same method described in Example 5 of British Pat. No. 1,219,360. The crude product may be purified by column chromatography of its chloroform solution through silicagel and by eluting with chloroform containing one percent of methanol. The compound recovered by evaporation of the chromatographed solution is 16, 17; 18, 19; 28, 29 hexahydro-3-formylrifamycin SV melting at 126°–131°C.

TABLE 1

| Example No. | R | Crystallization Solvent | Yield % | M.p. °C | C (calc. found) | H (calc. found) | N (calc. found) | Significative U.V. and visible bands $\mu$max | $E_{1\ cm}^{1\%}$ |
|---|---|---|---|---|---|---|---|---|---|
| 1 | $C_2H_5$ | ethyl acetate/ligroin | 62 | 214–215 | 62.48 / 61.55 | 6.82 / 7.14 | 3.64 / 3.36 | 470 / 325 | 182.8 / 283.6 |
| 2 | $C_3H_7$ | methanol | 86 | 181–183 | 62.90 / 63.19 | 6.95 / 6.90 | 3.57 / 3.51 | 468 / 326 | 191.2 / 299.2 |
| 3 | $i\text{--}C_3H_7$ | methanol | 86 | 229–231 | 62.90 / 62.58 | 6.95 / 7.12 | 3.57 / 3.70 | 468 / 327 | 177.9 / 279.9 |
| 4 | $C_4H_9$ | methanol | 74 | 220–222 | 63.30 / 63.45 | 7.08 / 7.11 | 3.51 / 3.67 | 468 / 326 | 176.9 / 281.8 |
| 5 | $C_5H_{11}$ | methanol | 93 | 200–202 | 63.68 / 63.62 | 7.20 / 7.23 | 3.45 / 3.75 | 468 / 325 | 173.2 / 274.7 |
| 6 | $C_8H_{17}$ | methanol | 80 | 188–190 | 64.76 / 65.03 | 7.56 / 7.69 | 3.28 / 3.47 | 475 / 329 | 142.6 / 234.6 |
| 7 | $C_{12}H_{25}$ | acetone/$H_2O$ | 46 | 95–104 | 66.06 / 65.57 | 7.98 / 8.09 | 3.08 / 3.25 | 480 / 330 | 138.3 / 223.5 |
| 8 | $C_9H_{19}$ | methanol | 70 | 177–181 | 65.11 / 65.18 | 7.67 / 7.78 | 3.23 / 3.35 | 480 / 330 | 156.0 / 250.0 |
| 9 | $CH_2CH_2OH$ | ethyl acetate | 60 | 200–204 | 61.21 / 60.42 | 6.67 / 6.98 | 3.56 / 3.90 | 470 / 325 | 183.0 / 279.0 |
| 10 | $CH(COOH)CH(CH_3)_2$ | benzene | 79 | 165–168 | 61.40 / 62.39 | 6.71 / 6.67 | 3.33 / 3.60 | 470 / 325 | 173.5 / 273.8 |
| 11 | $CH(COOH)CH_2CH(CH_3)_2$ | carbon tetrachloride | 30 | 168–171 | 61.81 / 60.61 | 6.84 / 6.81 | 3.28 / 3.19 | 470 / 325 | 157.0 / 259.0 |
| 12 | $CH(COOH)CH_2C_6H_5$ | carbon tetrachloride | 63 | 145–150 | 63.50 / 62.90 | 6.36 / 6.25 | 3.15 / 3.08 | 470 / 325 | 158.0 / 245.0 |
| 13 | $CH_2CH_2C_6H_5$ | ethyl acetate | 63 | 130–134 | 65.38 / 65.50 | 6.68 / 6.67 | 3.31 / 3.70 | 472 / 328 | 163.6 / 257.3 |
| 14 | $CH_2CH_2CH_2C_6H_5$ | methanol | 84 | 160–161 | 65.71 / 65.60 | 6.80 / 6.70 | 3.26 / 3.50 | 472 / 328 | 160.3 / 256.5 |
| 15 | $CH_2C_6H_4Br\text{--}p$ | methanol | 68 | 156–158 | 59.40 / 58.19 | 5.87 / 5.68 | 3.08 / 3.25 | 475 / 328 | 145.1 / 240.6 |
| 16 | $CH(C_6H_5)_2$ | methanol | 67 | 145–150 | 67.53 / 67.25 | 6.44 / 6.43 | 3.08 / 3.15 | 480 / 330 | 133.4 / 231.2 |
| 17 | $CH_2CH_2N\!\!<\!\!\square$  | ethanol | 39 | 162–168 | 63.07 / 61.72 | 7.10 / 7.35 | 5.02 / 4.67 | 472 / 327 | 167.0 / 250.0 |
| 18 | $CH_2CH_2N\!\!<\!\!\bigcirc$  | ethanol | 52 | >170 | 63.43 / 63.06 | 7.21 / 7.26 | 4.93 / 5.00 | 470 / 325 | 162.0 / 247.0 |
| 19 | $CH_2CH_2N\!\!<\!\!\bigcirc\!\!N$  | acetone | 6 | 187–188 | 62.34 / 62.11 | 7.21 / 7.39 | 6.46 / 6.25 | 470 / 325 | 158.0 / 251.0 |
| 20 | $(CH_2)_9 CH_3$ | light petroleum | 64 | 97–101 | 65.43 / 65.41 | 7.78 / 7.82 | 3.18 / 3.29 | 480 / 330 | 137.5 / 224.0 |
| 21 | $(CH_2)_6CH_3$ | ethyl acetate/light petroleum | 40 | 134–140 | 64.42 / 64.72 | 7.45 / 7.41 | 3.34 / 3.10 | 475 / 328 | 152.5 / 244.5 |
| 22 | $(CH_2)_7CH_3$ 25-desacetyl der. | methanol | 85 | 118–125 | 65.16 / 64.40 | 7.71 / 7.83 | 3.45 / 3.30 | 473 / 327 | 158.7 / 255.5 |
| 23 | $(CH_2)_5CH_3$ | ethyl acetate/light | 85 | 137–140 | 64.06 / 63.66 | 7.33 / 7.42 | 3.39 / 3.10 | 470 / 327 | 167.8 / 258.6 |

TABLE 1-continued

| Example No. | R | Crystallization Solvent | Yield % | M.p. °C | Analysis C (calc. found) | H | N | Significative U.V. and visible bands $\mu$max | $E_{1\ cm}^{1\%}$ |
|---|---|---|---|---|---|---|---|---|---|
| 24 | $(CH_2)_{10}CH_3$ | petroleum ligroin | 85 | 170–173 | 65.75 65.72 | 7.88 7.94 | 3.13 3.02 | 475 330 | 140.1 219.9 |
| 25 | $CH(C_3H_7)_2$ | methanol | 80 | 167–171 | 64.42 64.35 | 7.45 7.47 | 3.34 3.48 | 470 326 | 151.0 235.0 |
| 26 | $(CH_2)_3-CH=CH_2$ | methanol | 85 | 174–175 | 64.22 63.80 | 7.10 7.12 | 3.40 3.20 | 470 327 | 176.2 275.2 |
| 27 | $(CH_2)_7CH_3$ 16,17,18,19',28,29-hexahydro der. | ligroin | 50 | 85–92 | 64.31 64.00 | 8.21 8.19 | 3.26 3.43 | 477 330 | 125.5 209.6 |
| 28 | $CH_2-C=CH_2$ \| $C_2H_5$ | methanol | 80 | 163–165 | 63.84 63.05 | 6.98 7.02 | 3.46 3.69 | 472 327 | 183.6 280.9 |
| 29 | $CH_2-CH=CH-CH_3$ | methanol | 90 | 185–188 | 63.46 62.67 | 6.84 6.81 | 3.52 3.45 | 470 327 | 181.1 278.4 |
| 30 | $CH_2-CH=CH_2$ | methanol | 95 | 170–173 | 63.39 61.92 | 6.74 6.69 | 3.09 3.52 | 471 327 | 184.6 285.4 |
| 31 | $CH_2-C\equiv CH$ | methanol | 97 | 192–194 | 63.22 62.60 | 6.47 6.70 | 3.60 3.55 | 473 326 | 167.0 268.5 |
| 32 | $CH_2-CH=\overset{CH_3}{\underset{CH_3}{C}}-CH_2-CH_2-CH=\overset{CH_3}{\underset{}{C}}$ | methanol | 85 | 138–140 | 65.73 65.35 | 7.36 7.45 | 3.19 3.13 | 480 330 | 149.8 242.7 |
| 33 | cyclohexyl | methanol | 90 | 235–237 | 64.21 63.74 | 7.10 7.29 | 3.40 3.68 | 470 328 | 179.0 283.5 |
| 34 | $CH_2(CH=\overset{CH_3}{\underset{}{C}}-CH_2-CH_2)_2-CH=\overset{CH_3}{\underset{CH_3}{C}}$ | ligroin | 97 | 150–153 | 67.35 67.06 | 7.68 7.81 | 2.96 3.01 | 480 330 | 141.8 234.5 |
| 35 | $CH_2-CH_2-O-C_6H_5$ | methanol | 95 | 137–140 | 64.17 64.09 | 6.56 6.57 | 3.25 3.30 | 470 326 | 156.8 245.2 |
| 36 | $CH_2-CH_2-O-CH_3$ | methanol | 95 | 237–239 | 61.64 61.09 | 6.81 6.79 | 3.51 3.18 | 472 327 | 147.8 273.3 |
| 37 | $CH_2-CH_2-O-C_2H_5$ | methanol | 90 | 225–227 | 62.05 61.29 | 6.94 6.79 | 3.45 3.48 | 474 327 | 162.0 274.8 |
| 38 | $CH_2-CH_2-O-C_4H_9$ | methanol | 20 | 175–177 | 61.75 62.84 | 7.40 7.25 | 3.43 3.50 | 470 325 | 173.1 264.9 |
| 39 | $CH_2$-(2,4-dichlorophenyl) | methanol | 90 | 103–105 | 60.06 58.98 | 5.87 5.79 | 3.11 3.20 | 476 330 | 138.0 226.0 |
| | | | | | Cl 7.88 : 7.94 | | | | |
| 40 | $CH(CH_2)_4-CH_3$ \| $C_2H_5$ | methanol/water | 90 | 100–110 dec. | 64.77 64.61 | 7.56 7.80 | 3.28 3.38 | 475 328 | 149.5 206.8 |
| 41 | $CH-C_4H_9$ \| $C_3H_7$ | methanol/water | 95 | 102 dec. | 64.77 64.08 | 7.56 7.66 | 3.28 3.22 | 475 328 | 148.0 245.4 |
| 42 | $CH-C_4H_9$ \| $C_2H_5$ | methanol/water | 70 | 195 dec. | 64.42 64.47 | 7.45 7.59 | 3.34 3.45 | 472 327 | 167.2 270.4 |
| 43 | $CH-C_5H_{11}$ \| $CH_3$ | methanol | 90 | 133–136 | 64.42 63.70 | 7.45 7.43 | 3.34 3.25 | 475 328 | 165.6 266.7 |

Similarly, oximes of 3-formylrifamycin SV, 25-desacetyl-3-formylrifamycin SV and their derivatives hydrogenated in at least one of the positions 16, 17, 18, 19, 28 and 29 are prepared by condensation with a corresponding O-substituted hydroxylamine R-ONH$_2$ in which R is, for example, 4-hydroxybutyl
8-hydroxyoctyl
2-octen-4-yl
triphenylmethyl
tri-cyclopentylmethyl
cyclopentyl
2-propoxyethyl
2-benzyloxyethyl
3-ethoxypropyl
3-butoxypropyl
4-methoxybutyl
4-propoxybutyl
4-butoxybutyl
4-phenoxybutyl
6-phenoxyhexyl
2-dimethylaminoethyl
2-diethylaminoethyl 6-hydroxyhexyl
2-methyl-2-penten-3-yl
2-heptyn-1-yl
tri-cyclohexylmethyl
3-dibutylaminopropyl
cycloheptyl
2-isopropoxyethyl
3-methoxypropyl
3-propoxypropyl
3-benzyloxypropyl
4-ethoxybutyl
4-iso-propoxybutyl
4-iso-butoxybutyl
4-benzyloxybutyl
2-methylaminoethyl
2-ethylaminoethyl
2-dipropylaminoethyl 2-dibutylaminoethyl
3-dimethylaminopropyl
3-diethylaminopropyl
3-dibutylaminopropyl
4-diethylaminobutyl
4-dibutylaminobutyl
2-ethylphenylaminoethyl
2-(2-ethoxyethoxy)-ethyl
3-methoxybutyl
10-phenoxydecyl
2-(4-hydroxyphenoxy)-ethyl
4-carboxybenzyl
2,3,6-trichlorobenzyl
3-(4-carboxyphenyl)-propyl
2-(3,4-dichlorophenoxy)-ethyl
2-(2,6-dichlorophenoxy)-ethyl
3-(4-carboxyphenoxy)-propyl
3-(4-carboxymethoxyphenyl)-propyl
2-(2,6-dimethoxy-4-carboxyphenyl)-propyl
carboisobutoxymethyl
α-carbethoxybenzyl
3-(1-piperidino)-propyl
4-(2-furyl)-butyl
4-pyridylmethyl
3-(4-pyridyl)-propyl
3-(4-dimethylaminophenoxy)-propyl
5,6-dibromohexyl -continued 3-methylaminopropyl
3-ethylaminopropyl
3-dipropylaminopropyl
4-dimethylaminobutyl
4-dipropylaminobutyl
2-methylphenylaminoethyl
2-(2-methoxyethoxy)-ethyl
2-(2-butoxyethoxy)-ethyl
8-phenoxyoctyl
3-(4-hydroxyphenyl)-propyl
3-carboxy-3-phenylpropyl
2-carboxybenzyl
4-carboxyphenethyl
4-(4-carboxyphenoxy)-butyl 1-carboisobutoxyethyl
3-(3-nitro-4-hydroxyphenyl)-propyl
3-(2-thienyl)-propyl
2-(3-isoxazolyl)-ethyl
bis-(4-pyridyl)methyl
3-(8-quinolinoxy)-propyl In addition to the activities against microorganisms set forth hereinbefore certain of the compounds of the present invention have been found to be effective in inhibiting activity of DNA polymerases which are characteristics of human leukemic blood lymphoblasts and against typical nucleotidyl transferases (polymerases) of virus not utilized by the normal cell. It is known from studies on representative members of virus groups that they either carry or induce into the host cells polymerases as an essential part of their replication. Thus, there are viruses such as picorna viruses or polio viruses which induce RNA-dependent DNA-polymerase while other groups such as leukemia-sarcoma viruses carry a RNA-dependent DNA-polymerase. The presence and the very important role of the RNA-dependent DNA-polymerase reverse transcriptase in oncogenic RNA viruses has been discovered by D. Baltimore, Nature, 226, 1209 (1970) and by H. M. Temin et al., Nature, 226, 1211 (1970). Recent discovery of RNA-dependent DNA-polymerase enzyme in RNA tumor viruses of animal species has been confirmed also by other authors as it results for instance from the papers hereinbelow listed:

Green et al., Mechanism of carcinogenesis by RNA tumor viruses. I. An RNA-dependent DNA-polymerase in murine sarcoma viruses. Proc. Nat. Acad. Sci. USA 67, 385–393, 1970.

Spiegelman et al., Characterization of the products of RNA directed DNA-polymerase in oncogenic RNA viruses, Nature, London, 227, 563, 1970.

Hatanaka et al., DNA polymerase activity associated with RNA tumor viruses, Proc. Nat. Acd. Sci. USA, 67, 143, 1970.

Scolnick et al., DNA synthesis by RNA containing tumor viruses. Proc. Nat. Acad. Sci., USA, 67, 1034, 1970.

RNA virus implication in some tumors has been supported also by other facts: reverse transcriptase has been found to be present in particles from human milk obtained from women with a familiar history of breast cancer and from imbred population. (Scholn et al., Nature, 231, 97, 1971). Priori et al., (Nature, New Biology, 232, 16, 1971) isolated a virus named ESP-1 containing reverse transcriptase from cells from the pleural fluid of a child with lymphoma and have successfully grown it in tissue cultures. The presence in human breast cancer of RNA homologous to mouse mammary tumor virus RNA has been demonstrated through molecular hybridation experiments by R. Axel et al., (Nature, 235, 32, 1972).

At present there are no very effective drugs for treating viral diseases since viruses and cells have common metabolic requirements and pathway. The most promising approach to viral chemotherapy clearly is the design of suitable chemicals which combine specifically with viral or virus transformed cells polymerase but not with host cell polymerases controlling the expression of genetic information of viruses. Specific inhibitors of the viral or virus transformed cells enzymes and, in particular inhibitors of polymerases of RNA tumor viruses may have an important role in proving drugs for leukemia and other cancer therapy.

The inhibiting activity of the invention compounds has been tested on RNA dependent DNA polymerase of murine sarcoma virus (endogenous) and DNA dependent DNA polymerase activity of purified enzymes. The inhibition was tested according to the methods described by C. Gurgo et al., Nature, New Biology, 229, 111, 1971.

The effect of different concentrations of drugs on polymerase activity was determined by following 3H-dTTP (tritiated thymine deoxyriboside triphosphate) incorporation into the insoluble fraction. A typical example of the experimental procedures is the following: Isolation of virus and purification of viral polymerase Virus was isolated and purified from murine sarcoma virus (Moloney isolate) transformed rat cells (78Al cells) and murine sarcoma virus (Harvey isolate) transformed mouse cells (MEH cells) as previously described (Green et al., Proc. Nat. Acad. Sci. USA 67. 385–393, 1970, Rokutanda et al., Nature, 227, 1026–1028, 1970). The virion polymerase was purified 20–40 fold by incubation of purified virus with 0.5% NP-40 (nonidet P-40) in 0.1 M NaCl, 0.01 M Tris buffer (pH 7.6), 0.001 M EDTA for 5 minutes at room temperature and zonal centrifugration in 15-30% sucrose gradients in 10 mM (millimoles) sodium phosphate buffer (pH 7.4), 2.5 mM $MgCl_2$, 10 mM dithiothreitol, and 5% glycerol for 24 hours at 38.000 rpm in a Spinco SW41 rotor. The peak fractions of enzyme activity (13–17) of twenty-two fractions collected, were pooled, and stored at −70°C in 30% glycerol.

DNA polymerase assay

Enzyme incubation was performed for 1 hour at 37°C in 100 μl of reaction mixture containing 40 mM Tris buffer (pH 8.0), 5mM dithiothreitol, 30 mM NaCl, 2.5 mM MgCl$_2$, 0.1 mM daTP, dGTP, dCTP, and 10 μCi of $^3$H-dTTP (12–18 Ci/mmole) as described by Green et al., in Proc. Nat. Acad. Sci. US 67, 385–393, 1970. The reaction was terminated by the addition of 150 μl of 1N perchloric acid. Calf thymus DNA (100 μg) were added as carrier; the radioactive DNA product was processed as described in the two papers mentioned above.

Endogenous RNA dependent DNA polymerase activity was measured after the addition of 0.01% PN-40 to purified virus at the time of assay. The DNA polymerase activity of purified viral polymerase was measured with 2 μg of poly d(A-T) as template and no NP-40. Test for inhibition by rifamycin derivatives.

Rifamycin derivatives were dissolved in dimethylsulfoxide (DMSO) at a concentration of 5 mg/ml and stored at 4°C. Inhibition of the endogenous RNA dependent DNA polymerase activity was tested by adding 2 μl of derivative appropriately diluted in DMSO or 2 μl of DMSO (control) to the assay mixture prior to addition to disrupted virus which contained 15 to 30 μg of viral protein. Enzyme incubation was performed for 60 minutes at 37°C. Inhibition of purified enzyme was tested by pre-incubation of 2 μl of derivative of DMSO with 30 μl of enzyme (1 to 2 μg protein) for 10 minutes at 37°C; then 70 μl of substrate mixture were added and the mixture further incubated and processed as described above.

In representative tests the invention compounds described in Examples 4, 5, 6, 13, 14 and 16 at a concentration of 2–100 μg/ml or less reduced the incorporation of $^3$H-dTTP to less than 10 percent than found in the control tests clearly demonstrating inhibition of mechanism of carcinogenesis by RNA tumor viruses according to the most recent biochemical points of view.

The inhibiting effect of reverse transcriptase has been confirmed also by test on polymerase from murine leukemia virus. Murine leukemia virus RNA polymerase was prepared from TRITON X 100 disrupted virions as described by Gallo et al., Nature, New Biology, 232, 141 (1971). Virus of both Rauscher and Moloney types were previously purified by banding in the 1.16 g/ml region of a sucrose density gradient after initial low speed centrifugation to remove cellular debris and cushioning on 60% sucrose through 20% sucrose. Final concentration of virus preparation was at 10$^{11}$ particles/ml. As template endogenous 70S RNA was used. Concentrations of 50 μg/ml or less were found to be effective in inhibiting the enzyme.

For instance, inhibitions of about 50 percent were obtained with concentrations of only about 10–25 μg/ml of representative compounds 5, 6 and 14.

Similar results were found by using tumor cell polymerases of human origin. In this case the inhibiting activity was studied also on normal cells polymerases to characterize a selective effect. Representative rifamycin derivatives of formula I have been evaluated for their effects on two purified DNA polymerase isolated from (I) human normal (PHA stimulated) blood lymphocytes (2) a lymphoblast cell line (derived from a normal donor) and (3) human leukemic blood lymphoblast. Synthetic and/or native templates were used.

A typical example of the experimental procedure is the following:

Human Blood Lymphoblasts

Leukemic lymphoblasts were isolated from the peripheral blood of patients with acute lymphocytic leukemia (ALL) by leukophoresis. The cells were washed and erythrocytes removed by hypotonic lysis. Normal lymphocytes were obtained from the peripheral blood from healthy donors after removal of granulocytes by nylon column chromatography. They were stimulated with phytohemagglutinin (PHA) for 72 hours as described before (Gallo et al., Nature, 228, 927, 1970; Gallo et al. Science, 165, 400, 1968) in order to maximize DNA polymerase activity.

However, because of the logistic problems in obtaining sufficient amounts of these cells, a human "normal" tissue culture cell line (1788) was used to supply less purified DNA polymerases for some of the initial survey studies. Compounds of interest were then studied in more detail with the more purified enzymes from the normal and leukemic blood lymphocytes. These tissue culture cells were obtained from Associated Biomedic System, Inc.

DNA Polymerase Preparations

Cellular DNA polymerase were extracted and purified from normal blood (PHA stimulated) lymphocytes, and leukemic blood lymphocytes and 1788 lymphoid cells by homogenization in hypotonic buffer followed by Triton X 100 and/or high salt extraction of the extraylsosomal pellet. After differential centrifugation cellular extracts were further purified by DEAE cellulose, phosphocellulose, and Sephadex G 200 column chromatography. DNA polymerase Assays DNA polymerase assays were carried out in a final volume of 100 μl. The assay mixture contained Tris-HCl buffer, pH 8.3, 50 mM; MgAc, 6.0 mM; dithiothretiol, 8.0 mM; NaCl, 60 mM. Adjustment of pH was carried out after addition of inhibitors which were previously dissolved in dimethyl sulfoxide (DMSO). The final concentration of DMSO was 0.5% and all control samples included this amount of DMSO. An enzyme concentration that catalyzes an incorporation of approximately 1.0 pmole/hr was used in the assay. The enzyme was in most cases preincubated for 5 minutes with the inhibitor. The reaction was then initiated by the addition of template either synthetic DNA (poly d(AT) Miles Lab.) and DNA.RNA hybrid (oligo dT.poly rA), at 5 μg/ml or native templates; activated salmon sperm DNA at 50 μg/ml, and endogenous 70S viral RNA; 10 μCi of ($^3$H-methyl)TTP (New England Nuclear, 18.6 mCi/μmole, lyophilized and redissolved in 0.01 M HCl just prior to usage) and dATP (8 × 10$^{-5}$ M, with synthetic template) or all three deoxynucleoside triphosphates (8 × 10$^{-5}$ M with RNA or DNA templated reactions). In some experiments, there was no preincubation of enzyme with inhibitor.

In these cases reactions were initiated by adding enzyme to the complete reaction mixture which included the inhibitor. Samples were withdrawn at the start of incubation and after 30 minutes and terminated by the addition of 2 ml. of 0.08 M sodium pyrophosphate, and precipitated in 12.5% cold trichloroacetic acid (TCA) with yeast RNA (400 μg) as carrier. The products were collected on Millipore filter, washed extensively with 5% TCA and 1 ml. of DMSO-ethanol- 0.1 M NaCl mixture (0.5:70;29.5), dried and counted in 2 ml. of BBS₃ (Beckman) and 10 ml. of liquifluor (New England Nuclear) in a Packard liquid scintillation counter.

In representative experiments concentrations varying from 5 to 10 μg/ml of compounds of Examples 5,6 and 14 were found to provoke a 50% inhibition of leukemic polymerase with a synthetic DNA template. Reactions templated by a synthetic RNA template (poly rA.rU) were even more susceptible.

Representative experiments carried out with native template on normal and tumor cels polymerase showed a higher susceptibility of the tumor enzymes to the tested compounds.

Other biological characteristics dislayed by the new rifamycin derivatives include inhibition of focus formation on mouse, rat and human cells by the Moloney and Kirsten strain of murine sarcoma virus; selective inhibition of virus production by already transformed mouse and human cells; detection of revertant cells using the murine sarcoma virus transformed non-producer mouse and rat cell systems. The hydrazone compounds of the present invention have moreover confirmed their selective toxicity for virus transformed cells of mouse, rat and human origin when tested for colony forming ability.

In studies to determine the effect of the compounds in inhibiting focus formation by Moloney sarcoma virus on BALB/-3T3 cultures the following procedure is employed.

BALB/3T3 cell cultures are grown in 250 ml. plastic flasks in growth medium consisting of Eagle's minimal essential medium with 10% fetal bovine serum. Cell counts are made with a Coulter counter after suspending the cells with trypsin-EDTA and diluting in growth medium. Moloney murine sarcoma virus, as a tumor homogenate is employed. It is passaged four times in a Swiss-derived high passage mouse embryo cell line and assayed for focus-forming units in BALB/3T3 cells. In conducting the studies, a modificatiion of the method described by Hartley and Rowe, Proc. Nat. Acad. Sci. 55, 780, 1966 is used. In the present work, flasks are seeded with from 1–2 × 10⁶ cells in 25 ml. of growth medium and incubated at 37°C for 24 hours. Following the removal of fluids, virus at a predetermined number of focus forming units is introduced into 0.5 ml. of growth medium and allowed to adsorb on the monolayer of cells for 90 minutes at 37°C. Following this adsorption period, a predetermined quantity, usually as a dose rate of from about 5 to 10 μg/ml of a rifamycin compound (previously dissolved in dimethylsulfoxide at a concentration of 1 mg/ml) and carried in 25 ml. of growth medium, is added and the cultures returned to the incubator. As a control, dimethylsulfoxide alone in the growth medium is added to a separate culture. After three days inoculation, the cultures are fluid-changed and foci of transformed cells counted at day seven.

In this same method, vesicular stomatitis virus, New Jersey serotype is studied. Methods used to grow and assay this virus have been described by Hackett et al., Virology, 31, 114 (1967).

These properties indicate that these compounds possess an effective inhibitory activity on virus induced tumors in animals.

We claim:

1. O-Substituted oximes of 3-formylrifamycin SV having the formula

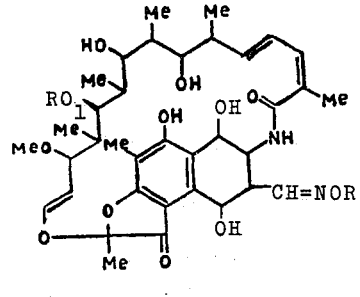

(I)

wherein R is selected from the group consisting of 4 to 12 carbon atom alkyl, 4 to 12 carbon atom alkenyl, propynyl, 2-heptyn-1-yl, cyclohexyl, cycloheptyl, 2-methoxyethyl, 2-ethoxyethyl, 2-propoxyethyl, 2-isopropoxyethyl, 2-butoxy-ethyl, 3-methoxypropyl, 3-ethoxypropyl, 3-propoxypropyl, 3-butoxypropyl, 3-methoxybutyl, 4-methoxybutyl, 4-ethoxy-butyl, 4-propoxybutyl, 4-isopropoxybutyl, 2-hydroxyethyl, 4-hydroxy-butyl, 6-hydroxyhexyl, 8-hdyroxyoctyl, 1-carboxyisobutyl, 1-carboxyisopentyl, carboisobutoxymethyl, 1-carboisobutoxyethyl, 2-phenoxy-ethyl, 4-phenoxybutyl, 6-phenoxyhexyl, 8-phenoxyoctyl, 10-phenoxydecyl, 2-(4-hydroxyphenoxy)ethyl, 2-(3,4-dichlorophenoxy)ethyl, 2-(2,6-dichlorophenoxy)ethyl, 3-(4-carboxyphenoxy)propyl, 3-(4-dimethylaminophenoxy)propyl, 4-(4-carboxyphenoxy)butyl, 2-benzyloxyethyl, 3-benzyloxypropyl, 4-benzyloxybutyl, 3-(8-quinolinoxy)propyl, 2-methylaminoethyl, 2-ethylaminoethyl, 3-methylaminopropyl, 3-ethylaminopropyl, 2-dimethylaminoethyl, 2-diethylaminoethyl, 2-dipropylaminoethyl, 2-dibutylaminoethyl, 3-dimethylaminopropyl, 3-diethylaminopropyl, 3-dipropylaminopropyl, 3-dibutylaminopropyl, 4-dimethylaminobutyl, 4-diethylaminobutyl, 4-dipropylaminobutyl, 4-dibutylaminobutyl, 4-bromobenzyl, 2,3,6-trichlorobenzyl, α-carbethoxybenzyl, 2-carboxybenzyl, α-phenylbenzyl, α,α-(diphenyl)benzyl, 4-carboxybenzyl, 2,4-dichlorobenzyl, 2-phenethyl, 3-phenylpropyl, 3-(3-nitro-4-hydroxyphenyl)propyl, 4-carboxyphenethyl, 3-(4-carboxymethoxyphenyl)propyl, 2-(2,6-dimethoxy-4-carboxy-phenyl)propyl, 3-carboxy-3-phenylpropyl, 4-carboxyphenethyl, α-carboxyphenethyl, 2-pyrrolidinylethyl, 2-piperidinylethyl, 2-(4-methylpiperazine-1-yl)ethyl, 3-(1-piperidino)propyl, 4-(2-furyl)butyl, 4-pyridylmethyl, 3-(4-pyridyl)propyl, 3-(2-thienyl)propyl, 2-(3-isoxazolyl)ethyl, bis-(4-pyridyl)methyl; R₁ is H or CH₃CO; and derivatives of the same oximes hydrogenated in the positions 16, 17; 18, 19; 28, 29.

2. O-Substituted oximes of 3-formylrifamycin SV as defined in claim 1 wherein R is 4 to 12 carbon atom alkyl.

3. O-Substituted oximes of 3-formylrifamycin SV as defined in claim 1 wherein R is mono- or poly-aryl substituted C₂ to C₈ alkyl of the group consisting of 2-phenethyl, 3-phenylpropyl, 3-(3-nitro-4-hydroxyphenyl)-propyl, 4-carboxyphenethyl, 3-(4-carboxymethoxyphenyl)-propyl, 2-(2,6-dimethoxy-4-carboxyphenyl)propyl, 4-carboxyphenethyl and 3-carboxy-3-phenylpropyl.

4. O-Substituted oximes of 3-formylrifamycin SV as defined in claim 3 wherein R is

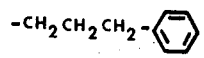
or
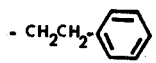
5. O-Substituted oximes of 3-formylrifamycin SV as defined in claim 1 wherein R is substituted benzyl of the group consisting of 4-bromobenzyl, 2,3,6-trichlorobenzyl, α-carbethoxybenzyl, 3-carboxybenzyl, α-phenylbenzyl, α,α-(diphenyl)benzyl, 4-carboxybenzyl and 2,4-dichlorobenzyl.
6. O-Substituted oximes of 3-formylrifamycin SV as defined in claim 5 wherein R is
* * * * *

UNITED STATES PATENT AND TRADEMARK OFFICE
CERTIFICATE OF CORRECTION

PATENT NO. : 3,933,800
DATED : January 20, 1976
INVENTOR(S) : Renato Cricchio and Giancarlo Lancini It is certified that error appears in the above-identified patent and that said Letters Patent are hereby corrected as shown below:

Page 1, formula of the Abstract should read:

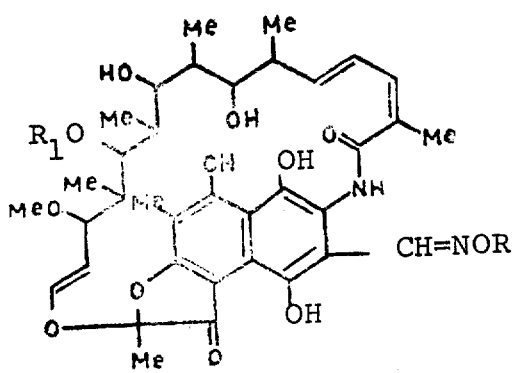

Column 1, line 5, "This is" should read --This application is--;

Column 1, line 33, "exhibit" should read --inhibit--;

Column 2, line 40, "3-formyltrifamycin" should read --3-formylrifamycin--;

Column 4, line 1, "of $PtO_2$ and" should read --of $PtO_2$ as--;

UNITED STATES PATENT AND TRADEMARK OFFICE
CERTIFICATE OF CORRECTION

PATENT NO. : 3,933,800
DATED : January 20, 1976
INVENTOR(S) : Renato Cricchio and Giancarlo Lancini It is certified that error appears in the above-identified patent and that said Letters Patent are hereby corrected as shown below:

Columns 3 and 4, Table I, last heading, "µ" should read --λ--;

Columns 3 and 4, Table I, Example No. 19 formula should read:

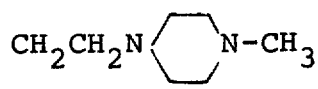

Columns 3 and 4, Table I, Example No. 23, under 2nd heading should read --ethyl acetate/light petroleum--;

Columns 5 and 6, Table I-continued, last heading, "µ" should read --λ--;

Column 5, Example No. 24, under 2nd heading, delete "petroleum";

Columns 5 and 6, Table I-continued, Example No. 27, should read --16, 17; 18, 19; 28, 29- --;

Columns 5 and 6, Table I-continued, Example No. 35, delete superscript "3" at beginning of formula;

Column 7, line 54, "Proc. Nat. Acd." should read --Proc. Nat. Acad.--;

UNITED STATES PATENT AND TRADEMARK OFFICE
CERTIFICATE OF CORRECTION

PATENT NO. : 3,933,800
DATED : January 20, 1976
INVENTOR(S) : Renato Cricchio and Giancarlo Lancini It is certified that error appears in the above-identified patent and that said Letters Patent are hereby corrected as shown below:

Column 8, line 51, "ing: Isolation of virus and purification of viral polymer-" should read --ing:--;

Column 8, line 52, "ase" should read --Isolation of virus and purification of viral polymerase--;

Column 8, line 63, "centrifugration" should read --centrifugation--;

Column 9, line 19, "NP-40. Test for inhibition by rifamycin derivatives." should read --NP-40.--;

Column 9, line 20 (additional line), should read --Test for inhibition by rifamycin derivatives--;

Column 9, line 42, "transcriptase" should read --transcriptases--;

Column 9, line 64, "polymerase" should read --polymerases--;

Column 10, line 32, "extraylsosomal" should read --extralysosomal--;

Column 10, line 35, "umn chromatography. DNA polymerase Assays" should read --umn chromatography.--;

Column 10, line 36, (additional line), should read --DNA polymerase Assays--;

Column 11, line 15, "dislayed" should read --displayed--;

UNITED STATES PATENT AND TRADEMARK OFFICE
CERTIFICATE OF CORRECTION

PATENT NO. : 3,933,800
DATED : January 20, 1976
INVENTOR(S) : Renato Cricchio and Giancarlo Lancini It is certified that error appears in the above–identified patent and that said Letters Patent are hereby corrected as shown below:

Column 14, line 3, "3-carboxylbenzyl," should read --2-carboxylbenzyl,--;

Signed and Sealed this

Twenty-fourth Day of August 1976

[SEAL]

Attest:

RUTH C. MASON
Attesting Officer

C. MARSHALL DANN
Commissioner of Patents and Trademarks